United States Patent [19]

Repine

[11] Patent Number: 5,679,532
[45] Date of Patent: Oct. 21, 1997

US005679532A

[54] SERUM FERRITIN AS A PREDICTOR OF THE ACUTE RESPIRATORY DISTRESS SYNDROME

[75] Inventor: John E. Repine, Englewood, Colo.

[73] Assignee: University Technology Corporation, Boulder, Colo.

[21] Appl. No.: 571,588

[22] Filed: Dec. 13, 1995

[51] Int. Cl.[6] .................. G01N 33/53; G01N 33/573; C12Q 1/32; C12Q 1/30
[52] U.S. Cl. .................. 435/7.1; 435/7.4; 435/26; 435/27; 435/975
[58] Field of Search .................. 435/7.1, 7.4, 26, 435/27, 975

[56] References Cited

U.S. PATENT DOCUMENTS

| | | | |
|---|---|---|---|
| 3,926,732 | 12/1975 | Rosen et al. | 195/103.5 R |
| 4,200,613 | 4/1980 | Alfrey et al. | 422/71 |
| 4,278,652 | 7/1981 | Niemann et al. | 424/1 |
| 4,560,648 | 12/1985 | Armenta | 435/7 |
| 5,147,783 | 9/1992 | Uda et al. | 435/7.23 |
| 5,196,311 | 3/1993 | Benson et al. | 435/7.94 |
| 5,202,264 | 4/1993 | Benson et al. | 435/7.94 |
| 5,389,522 | 2/1995 | Repine et al. | 435/7.4 |

OTHER PUBLICATIONS

Addison et al., "An Immunoradiometric Assay for Ferritin in the Serum of Normal Subjects and Patients with Iron Deficiency and Iron Overload," *J. Clin. Path.*, 25:326–329 (1972) month not available.

Al–Hassan et al., "Toxic Effects of the Soluble Skin Secretion From the Arabian Gulf Catfish (*Arius Thallasinus*, Ruppell) on Plasma and Liver Enzyme Levels," *Toxicon*, 23(3):532–534 (1985) month not available.

Allen et al., "Increased Membrane Binding of Erythrocyte Catalase in Hereditary Spherocytosis and in Metabolically Stressed Normal Cells," *Blood*, 49(1): 113–123 (Jan., 1977).

Anderson et al., "Serum Ferritin by a Rapid and Inexpensive ELISA Method," *Clinica Chimica Acta*, 116:405–408 (1981) month not available.

Annesley et al., "Cutaneous Thermal Burn and Oxidant-–Mediated Acute Lung Injury Appearance in Serum of Lung–Related Lactate Dehydrogenase Isoenzyme," *J. Free Radicals Biol. Med.*, 1(5–6):409–414 (1986) month not available.

Arosio et al., "Characterization of Serum Ferritin in Iron Overload: Possible Identity to Natural Apoferritin," *Brit. J. Haematol.*, 36:199–207 (1977) month not available.

Baldwin et al., "Oxidant Activity in Expired Breath of Patients with Adult Respiratory Distress Syndrome," *The Lancet*, vol. I(8471):11–14 (Jan. 4, 1986).

Balla et al., "Endothelial Cell Heme Oxygenase and Ferritin Induction By Heme Proteins: A Possible Mechanism Limiting Shock Damage," *Trans. Assoc. Amer. Physicians*, 105:1–6 (1992) month not available.

Balla et al., "Endothelial Cell Heme Oxygenase and Ferritin Induction in Rat Lung By Hemoglobin in Vivo," *Amer. J. Physiol.*, 268(2 pt. 1):L321–L327 (1995) month not available.

Bassett et al., "A Reversible Model of Acute Lung Injury Based on Ozone Exposure," *Lung*, 166(6):355–369 (1988) month not available.

Bernard et al., "Glutathione (GSH) Repletion by N–Acetylcysteine (NAC) in Patients with the Adult Respiratory Distress Syndrome (ARDS)," *Am. Rev. Respir. Dis.*, p. A221 (1989) (Abstract Only) month not available.

Bernard et al., "The American–European Consensus Conference on ARDS Definitions, Mechanisms, Relevant Outcomes, and Clinical Trial Coordination," *Am. J. Respir. Crit. Care Med.*, 149:818–824 (1994) month not available.

Bernard et al., "Report of the American–European Consensus Conference on ARDS: Definitions, Mechanisms, Relevant Outcomes and Clinical Trial Coordination," *Intensive Care Med.*, 20:225–232 (1994) month not available.

Beutler, *Red Cell Metabolism: A Manual of Biochemical Methods*, Grune & Stratton Inc., pp. 1–172 (1984) month not available.

Bloom et al., "Endotoxin and Pulmonary Cell Injury," *Surgery, Gynecology & Obstetrics*, 167(2):92–98 (Aug., 1988).

Brigham, K.L., "Oxidant Stress and Adult Respiratory Distress Syndrome," *Eur. Respir. J.*, 3, Suppl. 11:482s–484s (1990) month not available.

Brown et al., "Endotoxin Pretreatment Increases Endogenous Myocardial Catalase Activity and Decreases Ischemia-Reperfusion Injury of Isolated Rat Hearts," *Proc. Nat'l Acad. Sci.*, 86:2516–2520 (Apr., 1989).

Buhl et al., "Systemic Glutathione Deficiency in Symptom-Free HIV-Seropositive Individuals," *The Lancet*, vol. II(8675):1294–1298 (Dec. 2, 1989).

Carmel et al.. "Quantitative Determination of Ferritin by Electroimmunoassay," *Anal. Biochem.*, 85:499–505 (1978) month not available.

Carvalho et al., "Altered Factor VIII in Acute Respiratory Failure," *New England J. Med.*, 307:(18):1113–1119 (Oct. 28, 1982).

Cejka, J., "Enzyme Immunoassay for Factor VIII-Related Antigen," *Clin. Chem.*, 28(6):1356–1358 (1982) month not available.

Chopra et al., "Loss of $^{51}$Chromium, Lactate Dehydrogenase, and $^{111}$Indium as Indicators of Endothelial Cell Injury," *Laboratory Investigation*, 57(5):578–584 (1987) month not available.

Cochrane et al., "Pathogenesis of the Adult Respiratory Distress Syndrome," *J. Clin. Invest.*, 71:754–760 (Mar., 1983).

Conradie et al., "Quantitation of Serum Ferritin by Enzyme–Linked Immunosorbent Assay (ELISA)," *S. Africa Med. J.* 57:282–287 (Feb. 23, 1980).

Cook et al., "Evaluation of the Iron Status of a Population," *Blood*, 48(3):449–455 (Sep., 1976).

Day et al., "Gamma Glutamyl Transpeptidase in Rat Bronchoalveolar Lavage Fluid as a Probe of 4–Ipomeanol and Alpha Naphthylthiourea–Induced Pneumotoxicity," *Journal of Pharmacological Methods*, 24(1):1–8 (1990) month not available.

Donnelly et al., "Interleukin-8 and Development of Adult Respiratory Distress Syndrome in at–risk Patient Groups," *Lancet*, 341:643–647 (Mar. 13, 1993).

Duswald et al., "Released Granulocytic Elastase: An Indicator of Pathobiochemical Alterations in Septicemia After Abdominal Surgery," *Surgery*, 98(5):892–899 (Nov., 1985).

Fahmy et al., "Modulation of Iron Metabolism in Monocyte Cell Line U937 by Inflammatory Cytokines: Changes in Transferrin Uptake, Iron Handling and Ferritin mRNA," *Biochem J.* 296:175–181 (1993) month not available.

Fortier et al., "Enzyme–Labeled Immunosorbent Assay for Serum Ferritin: Method Evaluation and Comparison with Two Radioassays," *Clin. Chem.*, 25(8):1466–1469 (1979) month not available.

Fowler et al., "Adult Respiratory Distress Syndrome: Risk with Common Predispositions," *Ann. Intern. Med.*, 98:593–597 (May, 1983).

Gore, S.M., "Assessing Methods—Many Variables," *Brit. Med. J.*, 283:901–905 (Oct. 3, 1981).

Grum et al., "Plasma Xanthine Oxidase Activity in Patients with Adult Respiratory Distress Syndrome," *J. Crit. Care*, 2:22–26 (Mar., 1987).

Gutteridge et al., "Primary Plasma Antioxidants in Adult Respiratory Distress Syndrome Patients: Changes in Iron–Oxidizing, Iron–Binding, and Free Radical–Scavenging Proteins," *J. Lab. Clin. Med.*, 124(2):263–273 (Aug., 1994).

Halliwell et al., "Oxygen Free Radicals and Iron in Relation to Biology and Medicine: Some Problems and Concepts," *Archives of Biochemistry and Biophysics*, 246(2):501–514 (May 1, 1986).

Harlow et al., "Immunoassays," in *Antibodies A Laboratory Manual*, Cold Spring Harbor Laboratory, Cold Spring Harbor, New York pp. 578–612 (1988) month not available.

Henderson, R.F., "Use of Bronchoalveolar Lavage to Detect Lung Damage," *Environmental Health Perspectives*, 56:115–129 (Jun., 1984).

Hilgenfelt et al., "Relationship Between Angiotensinogen $\alpha_1$–Protease Inhibitor Elastase Complex, Antithrombin III and C–Reactive Protein in Septic ARDS," *Eur. J. Clin. Pharmacol.*, 38:125–131 (1990) month not available.

Hirayama et al., "Regulation of Iron Metabolism in HepG2 Cells: A Possible Role for Cytokines in the Hepatic Deposition of Iron," *Hepatology*, 18:874–880 (Oct., 1993).

Hoyt et al., "Murine Strain Differences in Acute Lung Injury and Activation of Poly(ADP–ribose) Polymerase by In Vitro Exposure of Lung Slices to Bleomycin," *American Journal of Respiratory Cell and Molecular Biology*, 7(6):645–651 (1992) month not available.

Hudson et al., "Clinical Risks for Development of the Acute Respiratory Distress Syndrome," *Am. J. Respir. Crit. Care Med.*, 151:293–301 (1995) month not available.

Hyers et al., "Tumor Necrosis Factor Levels in Serum and Bronchoalveolar Lavage Fluid of Patients with the Adult Respiratory Distress Syndrome," *Am. Rev. Respir. Dis.*, 144:268–271 (1991) month not available.

Kawaguchi et al., "Stimulation of Mn–Superoxide Dismutase Expression by Tumor Necrosis Factor–$\alpha$: Quantitative Determination of Mn–SOD Protein Levels in TNF–Resistant and Sensitive Cells by ELISA," *Biochem. Biophys. Res. Comm.*, 171(3):1378–1386 (Sep. 28, 1990).

Klausner et al., "Regulating the Fate of mRNA: the Control of Cellular Iron Metabolism," *Cell*, 72:19–28 (Jan. 15, 1993).

Knaus et al., "APACHE II: A Severity of Disease Classification System," *Crit. Care Med.*, 13(10):818–829 (Oct., 1985).

Kobune et al., "Interleukin–6 Enhances Hepatic Transferrin Uptake and Ferritin Expression in Rats," *Hepatology*, 19:1468–1475 (Jun., 1994).

Krsek–Staples et al., "Ceruloplasmin and Transferrin Levels are Altered in Serum and Bronchoalveolar Lavage Fluid of Patients with the Adult Respiratory Distress Syndrome," *Am. Rev. Respir. Dis.*, 145:1009–1015 (1992) month not available.

Kumazaki et al., "Assessment of the Permeability of the Pulmonary Microvasculature Using Radiotracers in a Case of Adult Respiratory Distress Syndrome," *Nippon Kyobu Shikkan Gakkai Zasshi (Japan)*, 29(2):258–262 (Feb., 1991) (Abstract Only).

Laurell, C., "Quantitative Estimation of Proteins by Electrophoresis in Agarose Gel Containing Antibodies," *Anal. Biochem.*, 15:45–52 (1966) month not available.

Leff et al., "Human Serum Catalase Decreases Endothelial Cell Injury from Hydrogen Peroxide," *J. Appl. Physiol.*, 71(5):1903–1906 (Jun., 1991).

Leff et al., "Increased Hydrogen Peroxide Scavenging and Catalase Activity in Serum From Septic Patients Who Subsequently Develop the Adult Respiratory Distress Syndrome (ARDS)," *American Review of Respiratory Disease* 143(4):A805 (1991) (Abstract Only) month not available.

Leff et al., "Increased Serum Catalase Activity in Septic Patients with the Adult Respiratory Distress Syndrome," *Am. Rev. Respir. Dis.*, 146:985–989 (1992) month not available.

Leff et al., "Progressive Increases in Serum Catalase Activity in Advancing Human Immunodeficiency Virus Infection," *Free Radical Biol. & Med.*, 13:143–149 (1992) month not available.

Leff et al. "Serum Antioxidants as Predictors of Adult Respiratory Distress Syndrome in Patients With Sepsis," *The Lancet*, 341:777–780 (Mar. 27, 1993).

Leff et al., "Serum Catalase Activity is Increased in Septic Patients and Predictive of Adult Respiratory Distress Syndrome (ARDS) Development," *Clinical Research*, 40(1):67A (Feb., 1992) (Abstract Only).

Lesnefsky et al., "Deferoxamine Pretreatment Reduces Canine Infarct Size and Oxidative Injury," *J. Pharm. & Exper. Therapeutics*, 253(3):1103–1109 (1990) month not available.

Linpisarn et al., "Sensitive Sandwich Enzyme Immunosassay for Serum Ferritin on Microtitre Plates," *Ann. Clin. Biochem.*, 18:48–53 (1981) month not available.

Litwin et al., "Immunolocytochemical Localization of Peroxisomal Enzymes in Human Liver Biopsies," *American Journal of Pathology*, 128(1):141–150 (Jul., 1987).

Marks et al., "Plasma Tumor Necrosis Factor in Patients with Septic Shock," *Am. Rev. Respir. Dis.*, 141:94–97 (1990) month not available.

Martin et al., "Paraquat–Induced Neutrophil Alveolitis Reduction of the Inflammatory Response by Pretreatment with Endotoxin and Hyperoxia," *Lung*, 164(2):107–120 (1986) month not available.

McCord, J., "The 'Irony' of Aging," in *Viewpoint*, A publication of the Webb–Warring Lung Institute, Denver, Colorado (Apr., 1992).

McGuire et al., "Studies on the Pathogenesis of the Adult Respiratory Distress Syndrome," *J. Clin. Invest.*, 69:543–553 (Mar., 1982).

McNeil et al., "Primer on Certain Elements of Medical Decision Making," *New Engl. J. Med.*, 293(5):211–215 (Jul. 31, 1975).

Miles et al., "Measurement of Serum Ferritin by a 2–Site Immunoradiometric Assay," *Anal. Biochem.*, 61:209–224 (1974) month not available.

Miller et al., "Iron–Independent Induction of Ferritin H Chain by Tumor Necrosis Factor," *Proc. Natl. Acad. Sci. USA*, 88:4946–4950 (Jun., 1991).

Montaner et al., "Multisystem Organ Failure Predicts Mortality of ICU Patients With Acute Respiratory Failure Secondary to AIDS–Related PCP," *Chest*, 102(6):1823–1828 (Dec., 1992).

Moore et al., "Penetrating Abdominal Trauma Index," *The Journal of Trauma*, 21(5):439–445 (1981) month not available.

Murray et al., "An Expanded Definition of the Adult Respiratory Distress Syndrome," *Am. Rev. Respir. Dis.*, 138:720–723 (1988) month not available.

Ogata et al., "Single Radial Diffusion Using Catalase Antibody as Screening Method of Hypocatalasemia," *Tohoku J. Exp. Med.*, 111:361–364 (1973) month not available.

Pacht et al., "Deficiency of Alveolar Fluid Glutathione in Patients with Sepsis and the Adult Respiratory Distress Syndrome," *Chest*, 100(5):1397–1403 (Nov., 1991).

Page et al., "Solid Phase ELISA for Serum Ferritin," *Scand. J. Clin. Lab. Invest.*, 40:641–645 (1980) month not available.

Parsons et al., "The Association of Circulating Endotoxin with the Development of the Adult Respiratory Distress Syndrome," *Am Rev. Respir. Dis.*, 140:294–301 (1989) month not available.

Pepe et al., "Clinical Predictors of the Adult Respiratory Distress Syndrome," *The American Journal of Surgery*, 144:124–130 (Jul., 1982).

Pickel et al., "AST, GLDH, Gamma–GT, Total Bilirubin and CPK During the First Week of Life in Prematurely Born Vital Calves and Calves with Respiratory Distress Syndrome," *J. Vet. Med. Ser. A*, 36(2):122–131 (1989) (German with English Abstract) month not available.

Pootrakul et al., "Quantitation of Ferritin Iron in Plasma, an Explanation for Non–Transferrin Iron," *Blood*, 71(4):1120–1123 (Apr., 1988).

Porter, F.S., "The Effect of Iron Content on the Behavior of Human Ferritin in an Inhibition–Type Radioimmunoassay," *J. Lab. Clin. Med.*, 83(1): 147–152 (Jan., 1974).

Prieto et al., "Serum Ferritin in Patients with Iron Overload and with Acute and Chronic Liver Diseases," *Gastroenterology* 68(3):525–533 (1975) month not available.

Reif, D.W., "Ferritin as a Source of Iron for Oxidative Damage," *Free Radical Biology & Medicine*, 12:417–427 (1992) month not available.

Repine et al., "Potential Mechanisms of Lung Injury from Hydroxyl Radical," *Chest*, 80:45s–48s (Jul. 1, 1981).

Repine et al., "Scientific Perspectives on Adult Respiratory Distress Syndrome," *The Lancet*, 339:466–469 (Feb. 22, 1992).

Rice et al., "$H_2O_2$ Injury Causes $Ca^{2+}$–Dependent and –Independent Hydrolysis of Phosphatidylcholine in Alveolar Epithelial Cells," *American Journal of Physiology* 263:L430–L438 (1992) month not available.

Rocker et al., "Diagnostic Criteria for Adult Respiratory Distress Syndrome: Time for Reappraisal," *The Lancet*, vol. I(8630):120–123 (Jan. 21, 1989).

Rogers, J.T., "Genetic Regulation of Iron Transport and Storage Genes: Links with the Acute Phase Response," *Iron and Human Disease*, Lauffler (ed.) CRC Press, Boca Raton, pp. 77–104 (1992) month not available.

Rogers et al., "Translational Control during the Acute Phase Response," *The Journal of Biological Chemistry*, 265(24):14572–14578 (Aug. 25, 1990).

Rubin et al., "Elevated von Willebrand Factor Antigen is an Early Plasma Predictor of Acute Lung Injury in Nonpulmonary Sepsis Syndrome," *J. Clin. Invest.*, 86:474–480 (Aug., 1990).

Seibert et al., "Hemoglobin Potentiates Oxidant Injury in Isolated Rat Lungs," *American J. Physiol.*, 260:H1980–1984 (1991) month not available.

Shapiro et al., "An Analysis of Variance Test for Normality (Complete Samples)," *Biometrika*, 52(3&4):591–611 (1965) month not available.

Siler et al., "Immunoreactive Interleukin–1 in Bronchoalveolar Lavage Fluid of High–Risk Patients and Patients with the Adult Respiratory Distress Syndrome," *Exp. Lung Res.*, 15:881–894 (May, 1989).

Silveira et al., "Application of an Enzyme–Linked Immunosorbent Assay (ELISA) to Von Willebrand Factor (vWF) and its Derivatives," *Thrombosis Research*, 43:91–102 (1986) month not available.

Smith et al., "Correlation of Bronchoalveolar Lavage Cell Populations with Clinical Severity of *Pneumocystis carinii* Pneumonia," *Chest* 92(1):60–64 (Jan., 1988).

Sturm (ed.), *Adult Respiratory Distress Syndrome*, Springer-Verlag Berlin Heidelberg, Germany, pp. 91–127, 193–211, 215–229, 230–244 (1991) month not available.

Sullivan et al., "Nutritional Iron Restriction Diminishes Acute Complement–Dependent Lung Injury," *Nut. Res.*, 9:625–634 (1989) month not available.

Suter et al., "High Bronchoalveolar Levels of Tumor Necrosis Factor and its Inhibitors, Interleukin–1, and Elastase, in Patients with the Adult Respiratory Distress Syndrome after Trauma, Shock or Sepsis," *Am. Rev. Resp. Dis.*, 145:1016–1022 (Oct. 28, 1992).

Taniguchi et al., "Clinical Significance of Superoxide Dismutases: Changes in Aging, Diabetes, Ischemia and Cancer," *Adv. Clin. Chem.*, 29:1–59 (1992) month not available.

Terada et al., "Hyperoxia and Self–or Neutrophil–Generated $O_2$ Metabolites Inactivate Xanthine Oxidase," *J. Appl. Physiol.*, 65(5):2349–2353 (Sep., 1988).

Theriault et al., "A Solid–Phase Enzyme Immunoassay for Serum Ferritin," *Clin. Chem.*, 23(11):2142–2144 (1977) month not available.

Van der Wal et al., "Effect of Iron Chelators on Paraquat Toxicity in Rats and Alveolar Type II Cells," *Am. Rev. Respir. Dis.*, 145:180–186 (1992) month not available.

Vreca et al., "Adenylate Kinase Activity in the Cerebrospinal Fluid of Hypoxic Newborns," *Clinical Biochemistry*, 22(2):135–139 (Apr., 1989).

Wang et al., "Protective Effect of Heat Shock Response on Oleic Acid–Induced Lung Injury in Rats," *Hunan Yike Daxue Xuebao*, 17(4):337–339 (1992) (Abstract Only) month not available.

Wang et al., "Protective Effect of Tungsten on Calcium Ionophore A–23187 Induced Injury in BPAEC," *Hunan Yike Daxue Xuebao*, 18(3):258–560 (1993) (Abstract Only) month not available.

Ward et al., "Systemic Complement Activation, Lung Injury, and Products of Lipid Peroxidation," *J. Clin. Invest.*, 76:517–527 (Aug., 1985).

Westcott et al., "Elevated Urinary Leukotriene $E_4$ Excretion in Patients with ARDS and Severe Burns," *Prostaglandins Leukotrienes and Essential Fatty Acids* 43(3):151–158 (1991) month not available.

White et al., "Cytokines Increase Rat Lung Antioxidant Enzymes During Exposure to Hyperoxia," *J. App. Physiol.*, 66(2):1003–1007 (1989) month not available.

Wieacker et al., "Assignment of the Gene Coding For Human Catalase to the Short Arm of Chromosome 11," *Ann. Genet.*, 23(2):73–77 (1980) month not available.

Wiemer et al., "Production and Characterisation of Monoclonal Antibodies Against Native and Disassembled Human Catalase," *Journal of Immunological Methods*, 151:165–175 (1992) month not available.

Wong et al., "Induction of Manganous Superoxide Dismutase by Tumor Necrosis Factor: Possible Protective Mechanism," *Science*, 242:941–944 (Nov., 1988).

Worwood, M., "Laboratory Determination of Iron Status," *Iron Metabolism in Health and Disease*, Brock et al. (eds.), WB Saunders Co., Ltd., London, pp. 450–476 (1995) month not available.

Worwood, M., "Serum Ferritin," *Meth. Haematol.*, vol. I, Cook (ed.), Churchill Livingston, New York, pp. 59–89 (1980) month not available.

Yurkov et al., "Tissue Hypoxia in Premature New Borns," *Pediatriya*, 0(1):12–14 (1980) (Abstract Only) month not available.

Zapol et al., (ed.), *Adult Respiratory Distress Syndrome.*, Marcel Dekker, Inc., New York, pp. 1–21, 23–36, 37–63, 77–89, 91–104 (1991) month not available.

Balla et al., "Ferritin: A Cytoprotective Antioxidant Strategem of Endothelium," *J. Biol. Chem.*, 267(25):18148–18153 (Sep. 5, 1992).

Connelly et al., "Serum Ferritin as a Predictor of the Acute Respiratory Distress Syndrome," *Am. J. Respir. Crit. Care Med.*, 155(1):21–25 (1997).

Mora et al., "Iron and Oxidative Injury in Isolated Perfused Rat Lungs," Meeting of the American Federation For Medical Research, Western Regional, Carmel, California, USA, Feb. 5–8, 1997, *J. Invest. Med.*, 45(1):156A (1997).

*Primary Examiner*—Gary L. Kunz
*Attorney, Agent, or Firm*—Marshall, O'Toole, Gerstein, Murray & Borun

[57] ABSTRACT

The invention relates to the discovery that serum ferritin concentrations are elevated in patients at risk for the development of Acute Respiratory Distress Syndrome (ARDS) and who subsequently develop ARDS, as compared to at-risk patients who do not subsequently develop ARDS. Thus, the invention includes a method for determining ARDS development potential in an at-risk patient comprising the steps of determining the patient's serum concentration of ferritin and determining ARDS development potential from said serum concentration of ferritin.

18 Claims, 4 Drawing Sheets

SERUM FERRITIN AS A PREDICTOR OF THE ACUTE RESPIRATORY DISTRESS SYNDROME

This invention was made with Government support under contract HL-40784 awarded by the National Institutes of Health. The Government has certain rights in this invention.

BACKGROUND OF THE INVENTION a. Field of the Invention

The present invention relates in general to methods and apparatus for performing assays for disease states, and more particularly to methods and apparatus for predicting the likelihood that a patient at risk for the development of acute respiratory distress syndrome will develop acute respiratory distress syndrome.

b. Background

The acute respiratory distress syndrome (ARDS; also known as the adult respiratory distress syndrome) is an inflammatory disorder characterized by the accumulation of neutrophils in the lung and the development of non-cardiogenic pulmonary edema [Repine, *Lancet* (1992); 339: 466–469]. ARDS is part of a spectrum of acute lung injury [Murray et al., *Am. Rev. Respir. Dis.* (1988); 138: 720–723; Bernard et al., *Am. J. Respir. Crit. Care Med.* (1994); 149: 818–824].

Once established, ARDS has an approximately 50% mortality, largely because there are still no specific treatments for the syndrome. Patients with major trauma, sepsis or other specific disorders are at risk for ARDS [Pepe et al., *Am. J. Surg.* (1982); 144: 124–130; Fowler et al., *Ann. Int. Med.* (1983); 98: 593–597; Hudson et al., *Am. J. Respir. Crit. Care. Med.* (1995); 151: 293–301], but the development of ARDS in any single, at-risk individual remains unpredictable.

Oxygen radicals are believed to be involved in the pathogenesis of ARDS [Repine (1992), supra; Brigham, *Eur. Respir. J.* (1990); 3, *Suppl* 11: 482s–484s]. Neutrophils and various physiological processes produce considerable amounts of superoxide anion ($O_2^-$) and secondarily, hydrogen peroxide ($H_2O_2$). Although these oxygen radical species have limited cytotoxicity themselves, they may react to form the highly toxic hydroxyl radical (.OH) in neutral body fluids in the presence of a transitional metal catalyst (usually iron) via the Haber-Weiss reaction:

$$Fe^{3+} + O_2^- \rightarrow Fe^{2+} + O_2$$
$$Fe^{2+} + H_2O_2 \rightarrow Fe^{3+} + OH + OH^-$$
$$\overline{O_2^- + H_2O_2 \rightarrow OH + OH^- + O_2}$$

Increasing the availability of free iron worsens acute lung injury, while decreasing iron availability reduces injury in animal models [Seibert et al., *Am. J. Physiol.* (1991); 260: H1980–1984; Sullivan et al., *Nut. Res.* (1989); 9: 625–634; Van der Wal et al., *Am. Rev. Respir. Dis.* (1992); 145: 18014 186].

Because only minute quantities of free iron are required for this catalytic enhancement of cytotoxic radical production, the availability of iron is tightly regulated to limit its toxicity. One physiological mechanism of iron regulation involves ferritin, a large (480 kD) intracellular iron storage protein which converts ferrous ($Fe^{2+}$) iron to the ferric ($Fe^{3+}$) state and sequesters up to 4500 iron atoms in the ferric state per molecule of ferritin. Ferritin also exists in the serum, and serum ferritin concentrations usually correlate with total body iron stores. Iron stored in ferritin is generally inaccessible for participation in the Haber-Weiss reaction. However, superoxide anion, acidosis, and nitric oxide can release iron from ferritin [Halliwell and Gutteridge, *Arch. Biochem. Biophys.* (1986); 246: 501–514; Reif, *Free Rad. Bio. Med.* (1992); 12: 417–427].

The major factor regulating ferritin synthesis is the availability of intracellular iron [reviewed in Klausner et al., *Cell* (1993); 72: 19–28; Rogers, "Genetic regulation of the iron transport and storage genes: links with the acute phase response." In *Iron and Human Disease*. Lauffer, editor. (1992); CRC Press, Boca Raton, pp. 77–104]. However, interleukin-1β and tumor necrosis factor-α also increase ferritin synthesis in cultured cells [Rogers (1992); Fohmy and Young, *Biochem. J.* (1993); 296: 175–181; Rogers et al., *J. Bio. Chem.* (1990); 265: 14572–14578; Hirayama et al., *Hepatology* (1993); 18: 874–880; Miller et al., *Proc. Natl. Acad. Sci. USA* (1991); 88: 4946–4950]. In addition, hepatic ferritin content and serum ferritin concentrations increase rapidly after administration of interleukin-6 to rats [Kobune et al., *Hepatology* (1994); 19: 1468–1475]. These effects of pro-inflammatory cytokines on ferritin synthesis are part of the hypoferremic response which occurs early in inflammation [Rogers (1992), supra].

Although numerous physiological conditions and disease states predispose a patient for ARDS (i.e., place a patient at risk for ARDS development), ARDS in fact develops relatively rarely in such patients [Fowler (1983), supra]. The ability to accurately and prospectively identify those at-risk patients in whom ARDS will develop will accelerate the emergence of new therapeutic modalities with the potential to prevent ARDS development or minimize its severity. For example, such an ability allows physicians to limit the number of patients needed for evaluation of novel ARDS therapeutic regimens, while at the same time increasing the accuracy with which therapeutic efficacy is evaluated. More generally, the ability to predict ARDS development facilitates clinical investigation into the pathophysiology of this ill-defined syndrome. Moreover, the ability to predict ARDS development in at-risk patients is useful for eliminating unnecessary medical treatments and reducing treatment costs for "at-risk" patients that are determined to have little likelihood of ARDS development. For all of these reasons, a long felt need exists for accessible and repeatable markers which predict the development of ARDS in at-risk patients [Donnelly et al., *Lancet* (1993); 341:643–647]. Preferably, such markers are measured non-invasively, e.g., without bronchoalveolar lavage.

Factor VIII has been identified as a predictor of ARDS and acute lung injury in septic patients [Carvalho et al., *N. Eng. J. Med.* (1982); 307(18):1113–1119; Rubin et al., *J. Clin. Invest.* (1990); 86:474–480]. On the whole, however, circulating plasma concentrations of mediators likely to be important in the pathogenesis of ARDS (e.g., C5a, endotoxin, tumor necrosis factor) have not proven useful as predictors of ARDS in at-risk patients [Donnelly et al. (1993), supra]. A need exists for additional markers which predict the development of ARDS in septic patients; for markers which predict the development of ARDS in non-septic patients at risk for the development of ARDS; and for additional markers which, in conjunction with previously-identified markers, enhance the ability to predict ARDS development in at-risk patients. Preferably such markers are measurable by a readily available and inexpensive procedure.

A limited number of serum markers have been identified which are useful for predicting ARDS development in certain patient populations. For example, U.S. Pat. No. 5,389,522, (Repine & Leff, inventors), which is incorporated herein by reference, discloses that the serum antioxidants manganese superoxide dismutase (MnSOD) and catalase predict ARDS development in septic patients with an efficiency (accuracy) of 83% and 69%, respectively. Co-pending U.S. patent application Ser. No. 08/347,290, filed Nov. 30, 1994 (Repine & Leff, inventors), discloses that serum levels of lactate dehydrogenase (LDH) predict ARDS development in septic patients with an efficiency (accuracy) of 75%. [See also Leff et al., Lancet (1993); 341:777–780.] Although these markers are useful in predicting septic patients who will develop ARDS, many cases of ARDS are still unpredicted, and ARDS sometimes is wrongly predicted. Accordingly, a need exists to provide tests that are even more sensitive, specific, and predictive of ARDS development in an "at-risk" patient population.

SUMMARY OF THE INVENTION

The present invention solves one or more of the aforementioned needs by identifying a new marker useful for predicting the development of ARDS in at-risk patients, by providing a method for accurately predicting the likelihood that a patient at risk for developing ARDS will in fact develop ARDS; and by providing an apparatus/kit for determining the ARDS development potential in an at-risk patient. The marker of the present invention may be used alone or in combination with other markers (e.g., MnSOD, catalase, LDH) that are useful in methods and kits for determining ARDS development potential in an at-risk patient.

The invention is based on the discovery that serum ferritin concentrations are greater in female ($p=0.003$) and male ($p=0.003$) at-risk patients who develop ARDS than in at-risk patients (of the same sex) who do not develop ARDS. As set forth below in greater detail, a serum ferritin concentration exceeding 270 nanograms per milliliter (ng/ml) in at-risk women predicted ARDS with an 83 percent sensitivity, 71 percent specificity, 67 percent positive and 86 percent negative predictive value, and an overall accuracy of 76%. In men, a serum ferritin concentration exceeding 680 ng/ml predicted ARDS with a 60 percent sensitivity, 90 percent specificity, 75 percent positive and 82 percent negative predictive value, and an overall accuracy of 80%. Serum ferritin concentrations did not correlate with C-reactive protein concentrations, were not significantly different in medical or surgical at-risk patients and were not accounted for by liver disease.

Thus, in one aspect the invention provides a method for determining acute respiratory distress syndrome (ARDS) development potential in a patient at risk for the development of ARDS comprising the steps of determining the patient's serum concentration of ferritin, comparing the patient's serum concentration of ferritin to a cut-off concentration of serum ferritin for the patient's sex, and determining ARDS development potential from the comparison, wherein serum concentrations of ferritin above the cut-off concentration for the patient's sex are predictive of (e.g., correlate with) ARDS development in the patient. Such a method is particularly useful for determining ARDS development potential in at-risk patients suffering from particular ARDS predisposing conditions, including sepsis, severe pancreatitis, recent hypertransfusion, recent aspiration, severe abdominal trauma, severe chest trauma, and multiple fractures.

The serum concentration of ferritin in at-risk patients who subsequently develop ARDS also has been discovered to be characteristically higher than that of healthy individuals not considered to be at risk for ARDS development, permitting one to determine ARDS development potential based on a comparison of an at-risk patient's serum concentration of ferritin to that of a healthy human subject. Thus, in another aspect, the present invention provides a method for determining a patient's potential for developing ARDS, the patient being of a predetermined sex, comprising the steps of determining the patient's serum concentration of ferritin, comparing the patient's serum concentration of ferritin to the serum concentration of ferritin of healthy human subjects having the same sex as the patient, and determining ARDS development potential from the comparison.

Figure 1A:
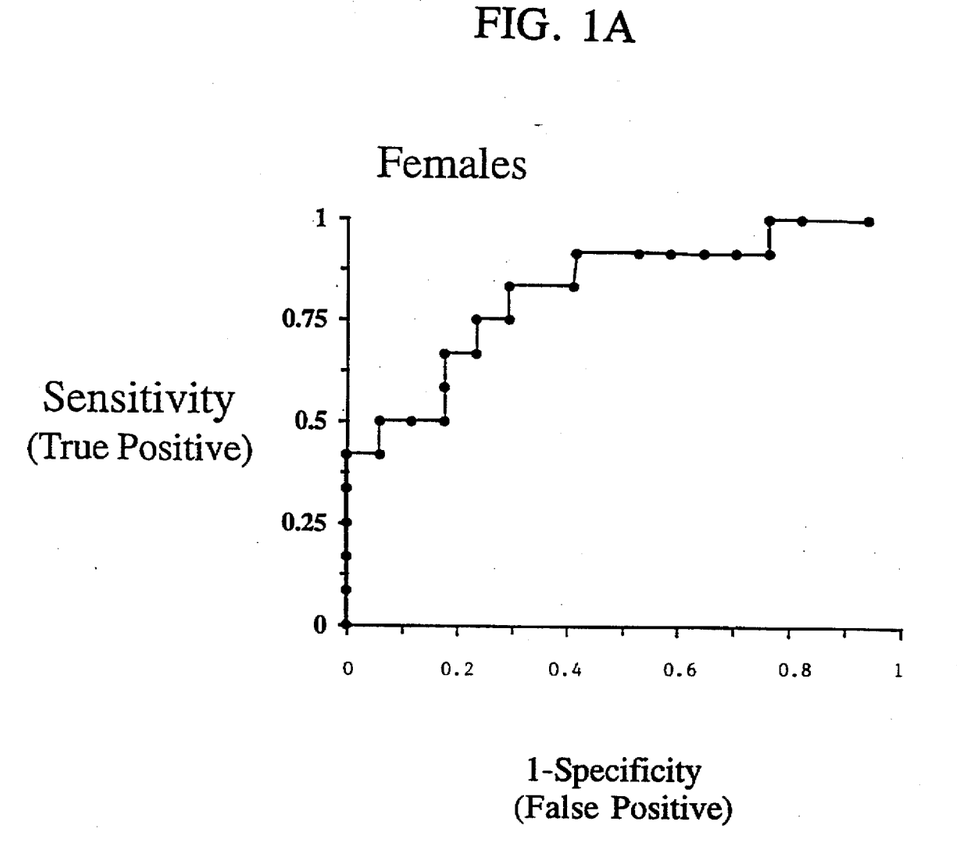
Figure 1B:
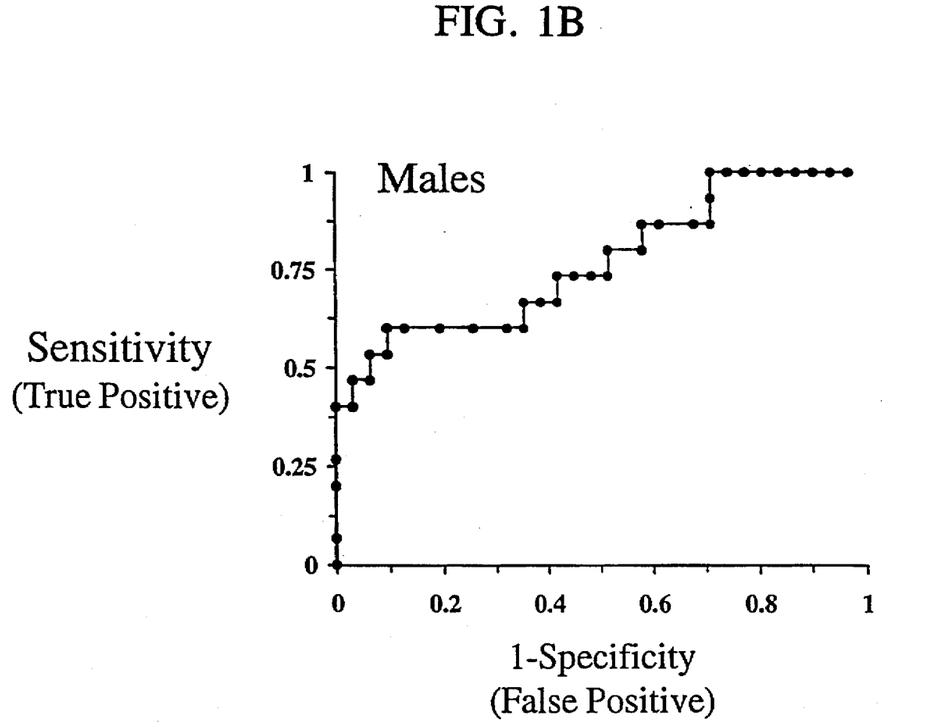

In a related aspect, the invention provides a kit for determining the ARDS development potential in an at-risk patient from the patient's serum. Such an apparatus includes a kit for determining serum ferritin concentration, such as a commercially-available ferritin antibody assay kit. The apparatus further includes a chart, table, graph, or the like for determining ARDS development potential from a patient's serum ferritin concentration, an exemplary graph being the receiver-operating characteristic curves provided herein.

Serum ferritin concentrations may be used in conjunction with other established ARDS markers or marker candidates to determine ARDS development potential. Thus, the invention provides a method for determining ARDS development potential in a patient at risk for the development of ARDS comprising the steps of: (a) determining the patient's serum concentration of ferritin, (b) determining the patient's serum level of at least one additional ARDS marker selected from the group consisting of manganese superoxide dismutase (MnSOD), catalase, lactate dehydrogenase (LDH), and Factor VIII antigen, and (c) determining ARDS development potential from said serum concentration of ferritin and said serum level of said additional selected ARDS marker or markers.

In a related aspect, the invention provides a kit for determining the ARDS development potential in an at-risk patient from the patient's serum. For example, the invention provides a kit comprising, in association, a kit of materials for determining serum ferritin concentration, and at least one additional kit of materials selected from the group consisting of (a) a kit for determining a serum level of MnSOD; (b) a kit for determining a serum level of LDH; (c) a kit for determining a serum level of Factor VIII antigen; and (d) a kit for determining a serum level of catalase.

Numerous other aspects and advantages of the present invention will be apparent upon the following detailed description thereof, reference being made to the drawing wherein:

BRIEF DESCRIPTION OF THE FIGURES

FIGS. 1A and 1B depict receiver-operating-characteristic curves for at-risk women and men, respectively. In FIG. 1A, the optimal serum ferritin cut-off concentration for at-risk women was 270 ng/ml, yielding a sensitivity of 83% and a specificity of 71%; and in FIG. 1B the optimal serum ferritin cut-off concentration for at-risk men was 680 ng/ml, yielding a sensitivity of 60% and a specificity of 90%.

DETAILED DESCRIPTION

In one aspect, the invention provides a method for determining acute respiratory distress syndrome (ARDS) development potential in a patient at risk for the development of ARDS comprising the steps of determining the patient's serum concentration of ferritin and determining ARDS development potential from the patient's serum concentration of ferritin. A determination of a patient's "ARDS development potential" is a determination of a likelihood (e.g., a probability) that the at-risk patient will in fact develop ARDS. The method includes a determination that an "at-risk" patient is unlikely to develop ARDS (i.e., has a low potential for developing ARDS), as well as a determination that an at-risk patient is likely to develop ARDS.

Procedures and materials for accurately determining a patient's serum concentration of ferritin are well-known in the art, and the step of determining the patient's serum concentration of ferritin may be performed using any such procedure known or developed for measurement of ferritin. In preferred methods, serum ferritin is measured immunologically, with a commercially available immunoassay, e.g., a radioimmunoassay (labeled ferritin), an immunoradiometric assay (labeled antibody), or an enzyme-linked immunosorbent assay (ELISA) [see generally Worwood, "Laboratory determination of iron status" in *Iron Metabolism in Health and Disease* (1995); Brock et al. (eds.), W B Saunders Co., Ltd., pp 455–458; and Worwood, "Serum ferritin." In: *Methods in Hematology*, Vol. 1 (1980); J. D. Cook (ed.), Churchill-Livingstone, New York, pp. 59–89].

The step of determining ARDS development potential from the selected patient's serum concentration of ferritin is performed by comparing the selected patient's serum concentration of ferritin to a cut-off concentration of serum ferritin, where serum concentrations of ferritin above the cut-off concentration are predictive of ARDS development in the patient. Thus, the invention provides a method for determining ARDS development potential in a patient at risk for the development of ARDS comprising the steps of: determining an at-risk patient's sex and serum ferritin concentration; comparing the patient's serum ferritin concentration to a cut-off concentration of serum ferritin for the patient's sex; and determining ARDS development potential from the comparison, where serum ferritin concentrations above the cut-off concentration of serum ferritin are predictive of ARDS development in the at-risk patient.

A "cut-off" concentration of serum ferritin is a serum ferritin concentration determined to be predictive of ARDS development when exceeded. As described herein, such a determination is made using, e.g., statistical analysis of serum ferritin concentration data collected from other at-risk patients (e.g., data collected from other at-risk patients whose serum ferritin has been measured and whose condition has been monitored to determine whether the patients developed ARDS or recovered without developing ARDS). The other at-risk patients may be the group of patients described herein or a portion thereof (e.g., the portion that consists of at-risk patients of the same sex as the selected patient); a group of patients that includes the group described herein or a portion thereof; or a completely different group of at-risk patients monitored by skilled practitioners in accordance with the teachings herein. Preferably, the cut-off concentration is statistically determined to have optimal discriminating value for ARDS development in the other at-risk patients (e.g., to have maximum sensitivity and specificity). However, certain serum ferritin concentrations other than the optimal discriminating concentration (e.g., above or below the optimal discriminating concentration) nonetheless are statistically predictive of ARDS, and therefore may be selected as a cut-off value. Using receiver-operating-characteristic curves such as those provided herein, or using other statistical summaries of serum ferritin concentration data collected from at-risk patients, the practitioner is capable of selecting a cut-off serum ferritin concentration having a desired level of sensitivity or specificity for predicting ARDS development. Considerations regarding the probability of ARDS development in the patient population and the costs (health costs and financial costs) associated with errors in diagnosis (both false-positive and false-negative) are understood to impact the selection of an appropriate cut-off serum ferritin concentration.

In addition to being characteristically higher than that of at-risk patients who do not subsequently develop ARDS, the serum concentration of ferritin in at-risk patients who subsequently develop ARDS also was discovered to be characteristically higher than that of healthy (normal) individuals not considered to be at risk for ARDS development. This discovery enables one to determine ARDS development potential based on a comparison of an at-risk patient's serum concentration of ferritin to that of a healthy human subject. Thus, in another aspect, the present invention provides a method for determining a patient's potential for developing ARDS, the patient being of a predetermined sex, comprising the steps of determining the patient's serum concentration of ferritin, comparing the patient's serum concentration of ferritin to the serum concentration of ferritin of healthy human subjects having the same sex as the patient, and determining ARDS development potential from the comparison.

In a related aspect, the invention also is directed to a kit for determining the ARDS development potential in an at-risk patient from the patient's serum. Such a kit includes materials for determining a serum ferritin concentration (e.g., from the serum of an at-risk patient) such as the materials in a commercially-available ferritin antibody assay kit. The kit further includes materials (e.g., a chart, table, graph, or the like) for determining ARDS development potential in an at-risk patient from the patient's serum ferritin concentration. A receiver-operating-characteristic curve, such as those provided herein, serves as an exemplary graph for inclusion in such an apparatus, because such curves provide a reference for the practitioner to determine a patient's likelihood of developing ARDS, based on the patient's serum concentration of ferritin. Similarly, one can prepare other graphical references, tables that correhte discrete serum ferritin concentrations with ARDS development potential, and the like according to the teachings herein. The chart, table, or graph, or the data contained therein, may be provided in computer-readable form (e.g., on a floppy disk or compact disk).

Serum ferritin concentrations alone provide a useful marker for determining ARDS development potential in at-risk patients, but in a related aspect of the invention serum ferritin concentrations are used in conjunction with other established ARDS markers or marker candidates to determine ARDS development potential. Thus, the invention provides a method for determining ARDS development potential in a patient at risk for the development of ARDS comprising the steps of: (a) determining the patient's serum concentration of ferritin, (b) determining the patient's serum level of at least one ARDS marker selected from the group consisting of manganese superoxide dismutase (MnSOD), catalase, lactate dehydrogenase (LDH), and Factor VIII antigen, and (c) determining ARDS development potential from said serum concentration of ferritin and said serum level of said selected ARDS marker or markers. By "serum level" is meant serum concentration and/or serum level of activity (i.e., enzymatic activity for selected markers that are enzymes), where appropriate. The determination of ARDS development potential from the serum concentration of ferritin and serum level of the additional marker(s) may be made by comparison to a cut-off concentration/level, comparison to a healthy human subject's concentration/level, or the like.

From the foregoing, it will be apparent that the invention also is directed to a kit for determining the ARDS development potential in an at-risk patient from the patient's serum. For example, the invention provides a kit comprising, in association, materials for determining serum ferritin concentration, and at least one of the following: (a) materials for determining a serum level of MnSOD; (b) materials for determining a serum level of LDH; (c) materials for determining a serum level of Factor VIII antigen; and (d) materials for determining a serum level of catalase. Preferably, the kit further includes one or more charts, tables, graphs, or the like for determining ARDS development potential from a serum ferritin concentration and from a selected serum level of the additional marker or markers.

Examples of materials and methods for assaying serum levels of individual markers are known in the art. For example, U.S. Pat. No. 5,147,783 (Uda et al., issued Sep. 15, 1992), which is incorporated herein by reference, provides immunological materials and methods for determining serum manganese superoxide dismutase (MnSOD) concentrations. In one embodiment, Uda et al. provides a kit for assaying human MnSOD comprising (a) a monoclonal antibody having very high specific immunoreactivity against human MnSOD, and (b) an enzyme-labelled monoclonal antibody (e.g., peroxidase-labelled, catalase-labelled, glucose oxidase labelled, β-galactosidase-labelled, alkaline phosphatase-labelled, etc.) having very high specific immunoreactivity against human MnSOD. Such a kit typically further includes a carrier for immobilizing the anti-(human MnSOD) antibody (e.g., plates, tubes, beads, or the like made from polyethylene, polystyrene, nitrocellulose, glass, or the like), a washing solution, a blocking solution, an enzyme substrate solution, and one or more standard MnSOD solutions of known concentration, for preparation of a calibration curve. Uda et al. further provides a method for assaying MnSOD concentrations, using the materials in such a kit. See also Kawaguchi et al., *Biochem. Biophys. Res. Comm.* (1990); 171(3):1378–1386.

U.S. Pat. No. 3,926,732 (Rosen et al., issued on Dec. 16, 1975), which is incorporated herein by reference, provides materials and methods for assaying catalase activity in a liquid such as blood serum. In one embodiment, the method comprises the steps of adding to the liquid a first reagent comprising a substance (e.g., a peroxide) which releases $H_2O_2$ in the presence of another substance (e.g., xanthine oxidase) in said liquid, adding to the liquid a second reagent oxidizable by $H_2O_2$ to yield a color reaction, said oxidation being inhibited by the presence of catalase, whereby said color reaction is stronger with a smaller catalase content of the liquid, and determining the catalase content with the aid of the hue of the color thus produced.

Leff et al., *J. Appl. Physiol.* (1991); 71(5):1903–1906, which is incorporated herein by reference, describes measurement of serum catalase activity polarographically as the rate of production of $O_2$ from $H_2O_2$. Serum (10 µl) or a catalase solution of known concentration is added to 400 µl of Hanks' balanced salt solution (GIBCO Labs, Grand Island, N.Y.) with 10 mM $H_2O_2$ in an airtight chamber equipped with a magnetic stirrer and maintained at 25° C. The rate of $O_2$ production is monitored with an electrode monitor (Yellow Springs Instruments, Yellow Springs, Ohio) coupled to a chart recorder.

Materials and methods for determining serum catalase concentration also are known in the art. Wiemer et al., *J. Immunol. Methods* (1992); 151:165–175, which is incorporated herein by reference, describes production of monoclonal antibodies immunoreactive with human catalase, such antibodies being useful in radioimmunoassays, immunoradiometric assays, enzyme-linked immunosorbent assays (ELISAs), and the like, for determining the concentration of catalase in a serum sample.

U.S. Pat. No. 5,196,311 (Benson et al., issued on Mar. 23, 1993), which is incorporated herein by reference, provides materials and methods for determining serum concentrations of Factor VIII-related antigen. In one embodiment, Benson et al. provides an ELISA kit comprising a polyclonal capture antibody against canine Factor VIII-related antigen, the antibody being raised in and isolated from a first vertebrate species (e.g., rabbit), a polyclonal sandwich antibody against canine Factor VIII-related antigen raised in and isolated from a second vertebrate species (e.g., goat), at least one standard solution of known Factor VIII-related antigen concentration, a control solution substantially free of Factor VIII-related antigen, and a reaction detector immunoglobulin (e.g., anti-(goat IgG) conjugated to a suitable detector, such as horseradish peroxidase enzyme, alkaline phosphatase enzyme, biotin, etc.).

U.S. Pat. No. 5,202,264 (Benson et al., issued on Apr. 13, 1993), which is incorporated herein by reference, provides additional materials and methods for determining serum concentrations of Factor VIII-related antigen. In particular, Benson et al. ('264) provides an antibody directed to Factor VIII-related antigen characterized by its immunological cross-reactivity with a Factor VIII-related antigen epitope that is evolutionarily conserved among vertebrate species. Benson et al. further provides materials and methods for measuring serum Factor VIII-related antigen using the antibody, including materials and methods for an ELISA as described above. In one basic embodiment, the method comprises contacting a serum sample with the antibody such that the Factor VIII-related antigen and the antibody form an immunoreactive complex, and detecting the antibody present in the complex.

Silveira et al., *Thrombosis Research* (1986); 43:91–102, which is incorporated herein by reference, describes a sandwich ELISA for measuring plasma Factor VIII-related antigen using rabbit anti-(human Factor VIII-related antigen) antibodies. The rabbit antibody is immobilized in the wells of a microtiter plate and acts as a reactive capture surface for Factor VIII-related antigen. Serially diluted plasma samples containing either known or unknown levels of Factor VIII-related antigen are reacted with the immobilized antibody, and then quantified by detection with a second (sandwich) antibody to human Factor VIII-related antigen (goat anti-(human factor VIII-related antigen)) and a horseradish peroxidase-conjugated porcine antigoat IgG. The peroxidase activity generated by the final antibody is proportional to the captured amount of Factor VIII-related antigen and is measured by the color change it catalyses in the substrate orthophenylenediamine (OPD). The color change reaction is subsequently quenched with sulfuric acid and the optical density measured to determine the concentration of Factor VIII-related antigen in the plasma tested.

Carvalho et al., *New Eng. J. Med.* (1992); 307(18):1113–1119, which is incorporated herein by reference, describes materials and methods for measurement of Factor VIII-related antigen by quantitative immunoelectrophoresis using an agarose gel containing commercially available rabbit anti-(human Factor VIII) antibody (Behring Diagnostics, Somerville, N.J.). Carvalho et al. further describes measurement of Factor VIII:C and Factor VII:vWF activity.

Cejka, *Clin. Chem.* (1982); 28(6):1356–58, which is incorporated herein by reference, describes materials and methods for quantification of Factor VIII-related antigen via enzyme-linked immunosorbent assay, using rabbit anti-(Factor VIII-related antigen) and horseradish peroxidase-labelled rabbit IgG to human Factor VIII-related antigen. Cejka obtained these antibodies from Dako (Copenhagen, Denmark) through Accurate Chemical and Scientific Corp., Westbury N.Y. 11590.

Beutler, *A Manual of Biochemical Methods* (1984); Grune & Stratton, Inc., pp. 65–66, which is incorporated herein by reference, describes materials and methods for determination of lactate dehydrogenase (LDH) activity. LDH catalyzes the reduction of pyruvate to lactate by NADH, and LDH activity is assayed by following the oxidation of NADH spectrophotometrically in a reaction mixture containing an appropriate buffer (e.g., Tris-HCl/EDTA), NADH, serum, water, and sodium pyruvate. The decrease in optical density at 340 nm (compared to a blank containing no sodium pyruvate) is measured.

Commercially available materials for measurement of serum LDH concentration are available from, e.g., Sigma Chemical Co., St. Louis, Mo. (anti-(human LDH) antibodies).

Materials and methods for solid phase sandwich enzyme immunoassays for ferritin are disclosed in Theriault et al., *Clin. Chem.*, 23(11):2142–2144 (1977); Fortier et al., *Clin. Chem.*, 25(8):1466–1469 (1979); Conradie et al. *S. Afr. Med. J.*, 57:282–287 (1980); Page et al., *Scand. J. Clin. Lab. Invest.*, 40:641–645 (1980); Anderson et al., *Clin, Chim. Acta.*, 116:405–408 (1981); and Linpisarn et al., *Ann. Clin, Biochem.*, 18:48–53 (1981), all of which are incorporated herein by reference.

Immunoassays for ferritin, which do not involve enzymes, include two-site immunoradiometric assays as disclosed in Addison et al., *J. Clin. Path.*, 25:326–329 (1972) and Miles et al., *Anal. Biochem.*, 61:209–224 (1974), competitive radioimmunoassays as disclosed in Porter, *J. Lab. Clin. Med.*, 83:147–152 (1974) and electroimmunoassays as disclosed in Carmel et al., *Anal. Biochem.*, 85:499–505 (1978) and Laurell, *Anal. Biochem.*, 15:45–52 (1966), all of which are incorporated herein by reference.

Also, U.S. Pat. No. 4,278,652 (Niemann et al., issued on Jul. 14, 1981), which is incorporated herein by reference, provides a process for the determination of ferritin in serum or in plasma, which comprises the steps of incubating an antibody directed against a first organ-specific isoferritin, which is covalently bound to polyamide 6,6 (nylon), on the one hand with ferritin standard solutions containing an isoferritin, and on the other hand with serum samples under the same conditions; decanting or aspirating the incubation solutions; washing the polyamide 6,6-isoferritin specific antibody/ferritin complex formed; incubating this complex with a $^{125}$I-labelled antibody directed against a second organ-specific isoferritin; decanting or aspirating the incubation solution; washing the polyamide 6,6-antibody/ferritin/antibody-$^{125}$I complex thereby formed; counting its radioactivity in a gamma counter; and comparing the radioactivities of the standard samples with those of the serum samples. Niemann et al. further provides a kit containing nylon beads to which anti-liver ferritin antibodies are bound; $^{125}$I-anti-placental ferritin antibodies; liver ferritin standard solutions; a serum diluent; and a buffer.

U.S. Pat. No. 4,560,648 (Armenia, issued on Dec. 24, 1985), which is incorporated herein by reference, provides materials (i.e., immunoassay kits) and methods for determining serum ferritin concentration. The important components of the kits include enzymatically-labelled ferritin (e.g., β-galactosidase-labelled ferritin), anti-ferritin antibodies (e.g., rabbit anti-(human ferritin) antibodies), and a chromogenic enzyme substrate.

Additionally, commercially available materials for the immunoassaying of serum ferritin (including anti-ferritin antisera) are available from, e.g., Sigma Chemical Co. (St. Louis, Mo.), ICN Biomedicals, Inc. (Costa Mesa, Calif.), and others. Additional materials and protocols for assaying serum ferritin concentration are described in greater detail below.

Numerous other aspects and advantages of the invention will be apparent from the following illustrative examples. Example 1 demonstrates that serum ferritin concentrations are useful for determining ARDS development potential in at-risk patients, and provides a determination of optimal discriminating serum ferritin concentrations for male and female patients, which are useful as cut-off serum ferritin concentrations for predicting ARDS development in at-risk patients. The remaining examples are prospective examples relating to additional aspects of the invention. Example 2 provides a protocol for the determination of an optimal battery of serum markers that, in combination, enhance the ability to predict the likelihood that an at-risk patient will develop ARDS. Example 3 provides a protocol to demonstrate the ARDS predictive value of ferritin concentration in bronchoalveolar lavage fluid (BALF) of patients at risk for ARDS development, alone or in combination with markers described in Examples 1 and 2.

EXAMPLE 1

The following procedure demonstrates that serum ferritin concentrations are useful for determining ARDS development potential in at-risk patients.

Patient Selection

Patients were studied using a protocol approved by the human subject review committee of the University of Colorado Health Science Center. Informed consent was obtained from each patient or a close relative. Seven categories of patients were defined to be at risk for the development of ARDS [Pepe et al. (1982), supra; Fowler et al. (1983), supra; Hudson et al. (1995), supra; Parsons et al., *Am. Rev. Respir. Dis.* (1989); 140: 294–301]. Patients were enrolled within 8 hours of fulfilling one of the seven criteria:

1. Sepsis: defined by evidence of a serious bacterial infection, with either a rectal or core temperature exceeding 39° C. or a peripheral leukocyte count exceeding 12,000 cells/ml or greater than 20% immature neutrophils. The diagnosis of sepsis also required at least one of the following: (a) a positive blood culture of a commonly accepted pathogen, (b) a strongly suspected or proven source of systemic infection, (c) gross pus in an enclosed space, (d) otherwise unexplained arterial hypotension (systolic blood pressure <80 mm Hg), (e) systemic vascular resistance <800 dyne/sec/cm$^2$, or (f) unexplained metabolic acidosis.

2. Severe pancreatitis: defined as pancreatitis complicated by one or more of the following: (a) white blood cell count >16,000 cells/mm$^3$; (b) lactate dehydrogenase >350 U/L (normal patient's LDH range: 100–210 U/L); (c) serum aspartate aminotransferase >250 U/L (normal patient's AST range: 9–36 U/L); (d) a fall of >10 percentage points in hematocrit; (e) initial arterial oxygen tension (PaO$_2$) <55 mm Hg while breathing room air; or (f) serum calcium <8.0 mg/dl.

3. Hypertransfusion: defined as requiring more than 10 units of whole blood or packed red blood cells in less than 24 hours.

4. Aspiration: defined as witnessed aspiration of gastric contents.

5. Severe abdominal trauma: defined by an abdominal trauma index exceeding 15 (determined at laparotomy) [Moore et al., *J. Trauma* (1981); 21: 439–445].

6. Severe chest trauma: defined by a flail chest or pulmonary contusion with PaO$_2$<70 mm Hg in patients receiving 40% or more supplemental oxygen.

7. Multiple fractures: defined as (a) unstable pelvic fracture requiting >6 units of whole blood or packed red blood cells, (b) 2 major long bone fractures (tibia, humerus or femur), or (c) a pelvic fracture plus a major long bone fracture.

Protocol

Within 6 hours of enrollment, each patient's blood was collected in a glass tube. Serum was separated from blood by centrifugation at 1000×g for 10 min. and stored at −70° C.

The following data were recorded at enrollment: (a) blood pressure, pulse, temperature, pulmonary artery pressures and cardiac output (when available); (b) respiratory support data (ventilator settings and parameters when applicable, supplemental O$_2$); (c) complete blood counts, serum electrolytes, blood urea nitrogen, creatinine; (d) chest radiograph interpretation; (e) transfusions; and (f) all culture data. APACHE II scores were calculated as a measure of severity of illness upon enrollment [see Knaus et al., *Crit. Care Med.* (1985); 13: 818–829]. A history of liver disease (defined as biopsy documented cirrhosis or chronic active hepatitis, history of esophageal or gastric variceal bleed, ascites attributed to liver disease, or acute hepatitis) or ethanol abuse was obtained from a retrospective chart review.

Patients were followed prospectively for the development of ARDS, which was defined when the following criteria were met simultaneously: (a) acute respiratory failure necessitating mechanical ventilation; (b) bilateral pulmonary infiltrates on chest radiograph; (c) pulmonary capillary wedge pressure below 18 mm Hg; (d) static pulmonary compliance below 50 ml/cm H$_2$O; and (e) arterial to alveolar partial pressure of oxygen ratio <0.25.

Additionally, data from eight patients (six sepsis, one aspiration pneumonia, one hypertransfusion) who fulfilled the diagnosis of ARDS prior to or at the time of enrollment were included for comparison purposes.

Ferritin assay:

Serum ferritin measurements are performed in most clinical laboratories, making this a readily available and relatively inexpensive test, easily implemented into practice.

Serum ferritin was assayed by a standard, commercially-available double antibody radioimmunoassay (Diagnostic Products Corporation, Los Angeles, Calif.) according to the manufacturer's instructions. Briefly patient serum was incubated for 1 hour with a known amount of I$^{125}$ human ferritin and rabbit anti-human ferritin antiserum. A precipitating solution containing goat anti-rabbit gamma globulin and dilute polyethylene glycol was then added, and the mixture was centrifuged at 3000×g for 15 minutes. The precipitate was analyzed on a gamma counter, and the results were compared to a calibration logit-log curve constructed with ferritin standards of known concentration. Data from 120 healthy control subjects was obtained from the manufacturer.

Other appropriate materials and methods for serum ferritin determination will be apparent to those of ordinary skill in the art, including immunoradiometric assays, enzyme-linked immunosorbent assays (ELISA), and other methods. Any such materials and methods are contemplated for use in the present invention.

C-reactive protein assay:

C-reactive protein was measured by rocket immunoelectrophoresis using a goat anti-human C-reactive protein antibody and a calibrated standard serum (Atlantic Antibodies, INCSTAR, Stillwater, Minn.)

Statistical analyses:

Since control values for ferritin are different in women and men, data was stratified by gender to perform statistical analyses. All data are presented as medians with 25%–75% quartiles because the values for serum ferritin were not distributed normally (Shapiro-Wilk test, p<0.0001) [Shapiro and Wilk, *Biometrika* (1965); 52:591–611]. Wilcoxon non-parametric analyses were utilized to analyze differences in serum ferritin concentrations. Receiver-operating characteristic (ROC) analyses were performed to determine the optimal threshold serum ferritin concentrations (i.e., to determine an optimal "operating position") for sensitivity and specificity [McNeil et al., *New Engl. J. Med.* (1975); 293:211–215]. Two by two contingency tables were created and analyzed with a Fisher's exact test [Campbell and Machin, *Medical Statistics: A Commonsense Approach* (1993); John Wiley and Sons, Chichester, Appendix I]. Sensitivity, specificity, positive and negative predictive values, and accuracy (defined as the true positive results plus true negative results divided by the total number of results) were then calculated [Forthofer and Lee, "Probability and life tables," in *Introduction to Biostatistics* (1995); Academic Press, San Diego, Chapter 5]. For each result, a 95% confidence interval for a binomial population was determined [Forthofer and Lee, supra, "Interval Estimation," Chapter 7]. Subsequently, a multivariate logistic regression model was employed in both multivariate analyses [Forthofer and Lee, supra, "Linear and Logistic Regression," Chapter 15; Gore, *Brit. Med. J.* (1981); 283:901–905]. An alpha level of 0.05 was used in all analyses.

Results

Serum ferritin concentrations were elevated both in female (p<0.0001) and male (p<0.0001) patients at-risk for the development of ARDS and in both female (p=0.001) and male (0=0.0009) patients with established ARDS when compared to values for healthy control subjects (Table I). In addition, the median serum ferritin concentration was greater (p=0.003) in female at-risk patients who subsequently developed the syndrome (referred to as "at-risk, pre-ARDS") than in clinically-indistinguishable at-risk female patients who did not progress to ARDS (referred to as "at-risk, non-ARDS") (Table II). Similarly, the median serum ferritin concentration in at-risk, pre-ARDS men was greater (p=0.003) than in clinically-indistinguishable at-risk, non-ARDS men (Table II). At-risk, pre-ARDS and at-risk, non-ARDS patients were similar (p>0.05) with respect to sex, age, race, predisposing diagnosis, and APACHE II scores (Table III). The incidence of ARDS in at-risk women (12/29) was 41 percent, while the incidence of ARDS in at-risk men (15/46) was 32 percent. Overall, ARDS developed in 36 percent of at-risk patients within 8 days of enrollment (range 6 hours–8 days). Certain raw data collected from patients is summarized in Table IV.

TABLE I

Serum Ferritin Concentrations in Healthy Subjects and Patients At-Risk For and With Established ARDS Ferritin Concentrations in ng/ml

| | Females | | Males | |
|---|---|---|---|---|
| Healthy Control Subjects | 31 (19–58)* (n = 58) | ⎤⎥ p < 0.0001 | 108 (60–181) (n = 62) | ⎤⎥ p < 0.0001 |
| At-Risk Patients | 280 (230–500) (n = 29) | ⎥ p = 0.001 | 480 (270–738) (n = 46) | ⎥ p = 0.0009 |
| Established ARDS Patients | 293 (180–758) (n = 4) | ⎦ | 1450 (928–3750) (n = 4) | ⎦ |

*Median (25–75% quartiles)
n = number of subjects/patients

TABLE II

Serum Ferritin Concentrations in At-Risk, Non-ARDS or At-Risk, Pre-ARDS Patients Ferritin Concentrations in ng/ml

| | Females | | Males | |
|---|---|---|---|---|
| At-Risk Non-ARDS Patients | 265 (182–310)* (n = 17) | ⎤⎥ p = 0.003 | 420 (225–550) (n = 31) | ⎤⎥ p = 0.003 |
| At-Risk Pre-ARDS | 490 (288–2600) (n = 12) | ⎦ | 925 (410–2000) (n = 15) | ⎦ |

*Median (25–75% quartiles)
n = number of patients

TABLE III

Demographic Data of At-Risk Pre-ARDS and At-Risk Non-ARDS Patients

| | Females | | | Males | | |
|---|---|---|---|---|---|---|
| | At-Risk Pre-ARDS (n = 12) | At-Risk Non-ARDS (n = 17) | P | At-Risk Pre-ARDS (n = 15) | At-Risk Non-ARDS (n = 31) | P |
| Age | 43.9 ± 13.7 | 51.8 ± 18.6 | 0.62 | 45.0 ± 12.2 | 42.0 ± 16.9 | 0.53 |
| Race | | | | | | |
| White | 4/12 (33%) | 9/17 (53%) | | 9/15 (60%) | 15/31 (48%) | |
| Hispanic | 4/12 (33%) | 5/17 (29%) | | 5/15 (33%) | 9/31 (29%) | 0.41 |
| Black | 3/12 (25%) | 2/17 (12%) | 0.70 | 1/15 (7) | 7/31 (23%) | |
| Native American | 1/12 (9%) | 1/17 (6%) | | | | |
| Diagnosis | | | | | | |
| Aspiration | 2/12 (17%) | 1/17 (6%) | | 1/15 (7%) | 3/31 (10%) | |
| Abdominal Trauma | 0/12 (0%) | 1/17 (6%) | | 3/15 (20%) | 8/31 (26%) | |
| Hypertransfusion | 1/12 (8%) | 4/17 (23%) | | 4/15 (26%) | 10/31 (32%) | |
| Multiple Fractures | 1/12 (8%) | 0/17 (0%) | 0.61 | 0/15 (0%) | 0/31 (0%) | 0.98 |

TABLE III-continued

Demographic Data of At-Risk Pre-ARDS and At-Risk Non-ARDS Patients

| | Females | | | Males | | |
|---|---|---|---|---|---|---|
| | At-Risk Pre-ARDS (n = 12) | At-Risk Non-ARDS (n = 17) | P | At-Risk Pre-ARDS (n = 15) | At-Risk Non-ARDS (n = 31) | P |
| Pancreatitis | 1/12 (8%) | 1/17 (6%) | | 1/15 (7%) | 2/31 (6%) | |
| Chest Trauma | 0/12 (0%) | 0/17 (0%) | | 1/15 (7%) | 1/31 (3%) | |
| Sepsis | 7/12 (59%) | 10/17 (59%) | | 5/15 (33%) | 7/31 (23%) | |
| APPACHE II Score | 14.5 ± 4.5 | 15.8 ± 4.8 | 0.44 | 14.0 ± 6.2 | 12.2 ± 4.7 | 0.30 |

TABLE IV

| Patient Number | Sex (M/F) | ARDS Risk Condition | Serum Ferritin Concentration | APACHE II Score | Developed ARDS (Y/N) |
|---|---|---|---|---|---|
| A.R. #1 | M | Sepsis | 520 | 16 | Yes |
| A.R. #2 | F | Sepsis | 270 | 16 | Yes |
| A.R. #3 | M | Sepsis | 3600 | 13 | Yes |
| A.R. #4 | M | Sepsis | 1800 | 6 | Yes |
| A.R. #5 | M | Aspiration | 2150 | 11 | Yes |
| A.R. #6 | M | Sepsis | 265 | 13 | Yes |
| A.R. #7 | M | Hyper-transfusion | 270 | 11 | Yes |
| A.R. #8 | M | Pancreatitis | 380 | 2 | Yes |
| A.R. #9 | M | Hyper-transfusion | 115 | 11 | No |
| A.R. #10 | M | Hyper-transfusion | 390 | 13 | No |
| A.R. #11 | M | Hyper-transfusion | 200 | 16 | No |
| A.R. #12 | M | Aspiration | 425 | 4 | No |
| A.R. #13 | F | Abdominal Trauma | 300 | 17 | No |
| A.R. #14 | F | Hyper-transfusion | 390 | 7 | Yes |
| A.R. #15 | M | Abdominal trauma | 180 | 7 | No |
| A.R. #16 | M | Aspiration | 230 | 14 | No |
| A.R. #17 | M | Hyper-transfusion | 225 | 10 | No |
| A.R. #18 | F | Hyper-transfusion | 400 | 11 | No |
| A.R. #19 | M | Hyper-transfusion | 120 | 16 | No |
| A.R. #20 | F | Sepsis | 265 | 19 | No |
| A.R. #21 | F | Sepsis | 145 | 14 | No |
| A.R. #22 | M | Abdominal Trauma | 460 | 10 | No |
| A.R. #23 | F | Aspiration | 140 | 23 | No |
| A.R. #24 | F | Sepsis | 145 | 16 | No |
| A.R. #25 | M | Abdominal Trauma | 500 | 8 | No |
| A.R. #26 | M | Hyper-transfusion | 105 | 12 | No |
| A.R. #27 | M | Sepsis | 560 | 17 | No |
| A.R. #28 | F | Pancreatitis | 420 | 6 | No |
| A.R. #29 | M | Sepsis | 270 | 7 | No |
| A.R. #30 | M | Abdominal trauma | 520 | 15 | No |
| A.R. #31 | M | Sepsis | 880 | 7 | No |
| A.R. #32 | F | Pancreatitis | 315 | 12 | Yes |
| A.R. #33 | F | Multiple fractures | 160 | 14 | Yes |
| A.R. #34 | M | Abdominal trauma | 1800 | 10 | Yes |
| A.R. #35 | M | Hyper-transfusion | 1050 | 16 | Yes |
| A.R. #36 | M | Abdominal trauma | 550 | 11 | No |
| A.R. #37 | M | Sepsis | 430 | 20 | No |
| A.R. #38 | M | Pancreatitis | 1000 | 2 | No |
| A.R. #39 | M | Abdominal trauma | 150 | 12 | No |
| A.R. #40 | M | Sepsis | 1250 | 11 | No |
| A.R. #41 | M | Abdominal trauma | 2000 | 19 | Yes |
| A.R. #42 | M | Hyper-transfusion | 560 | 13 | No |
| A.R. #43 | M | Sepsis | 125 | 11 | No |
| A.R. #44 | M | Hyper-transfusion | 365 | 10 | No |
| A.R. #45 | F | Sepsis | 320 | 19 | No |
| A.R. #46 | F | Sepsis | 240 | 23 | No |
| A.R. #47 | F | Sepsis | 580 | 14 | Yes |
| A.R. #48 | M | Hyper-transfusion | 550 | 14 | No |
| A.R. #49 | F | Sepsis | 155 | 17 | No |
| A.R. #50 | M | Abdominal Trauma | 925 | 20 | Yes |
| A.R. #51 | M | Abdominal Trauma | 680 | 9 | No |
| A.R. #52 | M | Hyper-transfusion | 390 | 19 | No |
| A.R. #53 | F | Hyper-transfusion | 250 | 19 | No |
| A.R. #54 | F | Hyper-transfusion | 265 | 23 | No |
| A.R. #55 | M | Pancreatitis | 420 | 17 | No |
| A.R. #56 | M | Aspiration | 300 | 13 | No |
| A.R. #57 | M | Hyper-transfusion | 480 | 12 | Yes |
| A.R. #58 | F | Hyper-transfusion | 210 | 12 | No |
| A.R. #59 | M | Chest Trauma | 540 | 17 | No |
| A.R. #60 | M | Abdominal trauama | 300 | 11 | No |
| A.R. #61 | M | Sepsis | 480 | 24 | No |
| A.R. #62 | M | Hyper-transfusion | 410 | 14 | Yes |
| A.R. #63 | M | Chest Trauma | 690 | 28 | Yes |
| A.R. #64 | F | Sepsis | 2750 | 15 | Yes |
| A.R. #65 | M | Sepsis | 2150 | 19 | Yes |
| A.R. #66 | F | Sepsis | 5000 | 15 | Yes |
| A.R. #67 | F | Sepsis | 270 | 12 | No |
| A.R. #68 | F | Aspiration | 4400 | 20 | Yes |
| A.R. #69 | F | Sepsis | 400 | 16 | Yes |
| A.R. #70 | F | Sepsis | 220 | 11 | Yes |
| A.R. #71 | F | Aspiration | 280 | 6 | Yes |
| A.R. #72 | F | Sepsis | 620 | 15 | No |
| A.R. #73 | F | Sepsis | 1800 | 19 | Yes |
| A.R. #74 | F | Sepsis | 2150 | 20 | Yes |
| A.R. #75 | F | Sepsis 270 | 13 | No | |
| ARDS #1 | M | (N/A) | 4400 | 29 | (N/A) |
| ARDS #2 | F | (N/A) | 900 | 29 | (N/A) |
| ARDS #3 | M | (N/A) | 870 | 11 | (N/A) |

TABLE IV-continued

| Patient Number | Sex (M/F) | ARDS Risk Condition | Serum Ferritin Concentration | APACHE II Score | Developed ARDS (Y/N) |
|---|---|---|---|---|---|
| ARDS #4 | M | (N/A) | 1100 | 16 | (N/A) |
| ARDS #5 | F | (N/A) | 330 | 12 | (N/A) |
| ARDS #6 | M | (N/A) | 1800 | 8 | (N/A) |
| ARDS #7 | F | (N/A) | 255 | 7 | (N/A) |
| ARDS #8 | F | (N/A) | 155 | 16 | (N/A) |

A.R. = At-risk patient
ARDS = Patient with established ARDS at beginning of study
(N/A) = Not applicable Receiver-operating-characteristic (ROC) curves were constructed to determine the clinical significance of serum ferritin concentration, and the optimal discriminating value of serum ferritin concentration as a determinant of ARDS development potential. In women, a serum ferritin value of 270 ng/ml was selected (FIG. 1A). This value was 8 times the median concentration of healthy control females. Using a two-tailed Fisher's Exact test, the incidence of ARDS was greater in women with a serum ferritin concentration >270 ng/ml than in women with a serum ferritin concentration ≦270 ng/ml (67 percent versus 14 percent; p=0.0078)). Employing a serum ferritin concentration of 270 ng/ml as a threshold (cut-off concentration) in women at risk for the syndrome, ARDS was predicted with a sensitivity of 83 percent (95 percent confidence interval, 62–100 percent) and a specificity of 71 percent (95 percent confidence interval, 49–93 percent). The positive and negative predictive values were 67 percent (95 percent confidence interval, 43–91 percent) and 86 percent (95 percent confidence interval, 68–100 percent), respectively. The accuracy of the serum ferritin test was 76 percent (95 percent confidence interval, 68–100 percent) (Table V).

A serum ferritin concentration of 680 ng/ml was selected in men (FIG. 1B). This value was 6.5 times the median serum ferritin concentration of healthy control males. Using a two-tailed Fisher's exact test, the incidence of ARDS was greater in men with a serum ferritin concentration >680 ng/ml when compared to men with a serum ferritin concentration of <680 ng/ml (75 percent versus 18 percent; p=0.0006). Employing a serum ferritin concentration of 680 ng/ml as a threshold (cut-off concentration), ARDS was predicted in at-risk men with a sensitivity of 60 percent (95 percent confidence interval, 35–84 percent), a specificity of 90 percent (95 percent confidence interval, 70–100 percent, and positive and negative predictive values of 75 percent (95 percent confidence interval, 50–100 percent) and 82 percent (95 percent confidence interval, 69–95 percent), respectively. The accuracy of the serum ferritin test was 80 percent (95 percent confidence interval, 68–92 percent) (Table V).

TABLE V

ARDS Predictive Values of Serum Ferritin Concentrations in At-Risk Patients

| | >270 ng/ml in Females (n = 29) | | >680 ng/ml in Males (n = 46) | |
|---|---|---|---|---|
| Test | Percentage | 95% Confidence Interval | Percentage | 95% Confidence Interval |
| Sensitivity | 83% | (62–100%) | 60% | (35–84%) |
| Specificity | 71% | (49–93%) | 90% | (70–100%) |
| Positive Predictive Value | 67% | (43–91%) | 75% | (50–100%) |
| Negative Predictive Value | 86% | (68–100%) | 82% | (69–95%) |
| Accuracy | 76% | (68–100%) | 80% | (68–92%) |

There were no significant differences in serum ferritin concentrations between medical patients compared with surgical patients (mainly trauma patients, although some surgical patients developed sepsis) in either women [medical: 298 ng/ml (25–75 percent quartiles, 243–610) versus surgical: 265 ng/ml (25–75 percent quartiles, 185–345); p=0.297] or men [medical: 453 ng/ml (25–75 percent quartiles, 269–1063) versus surgical: 490 ng/ml (25–75 percent quartiles, 316–650); p=0.80]. The median serum ferritin values appear similar in medical and surgical groups. To confine this conclusion statistically, repetition of the foregoing study to provide data from additional patients is required.

Figure 2A:
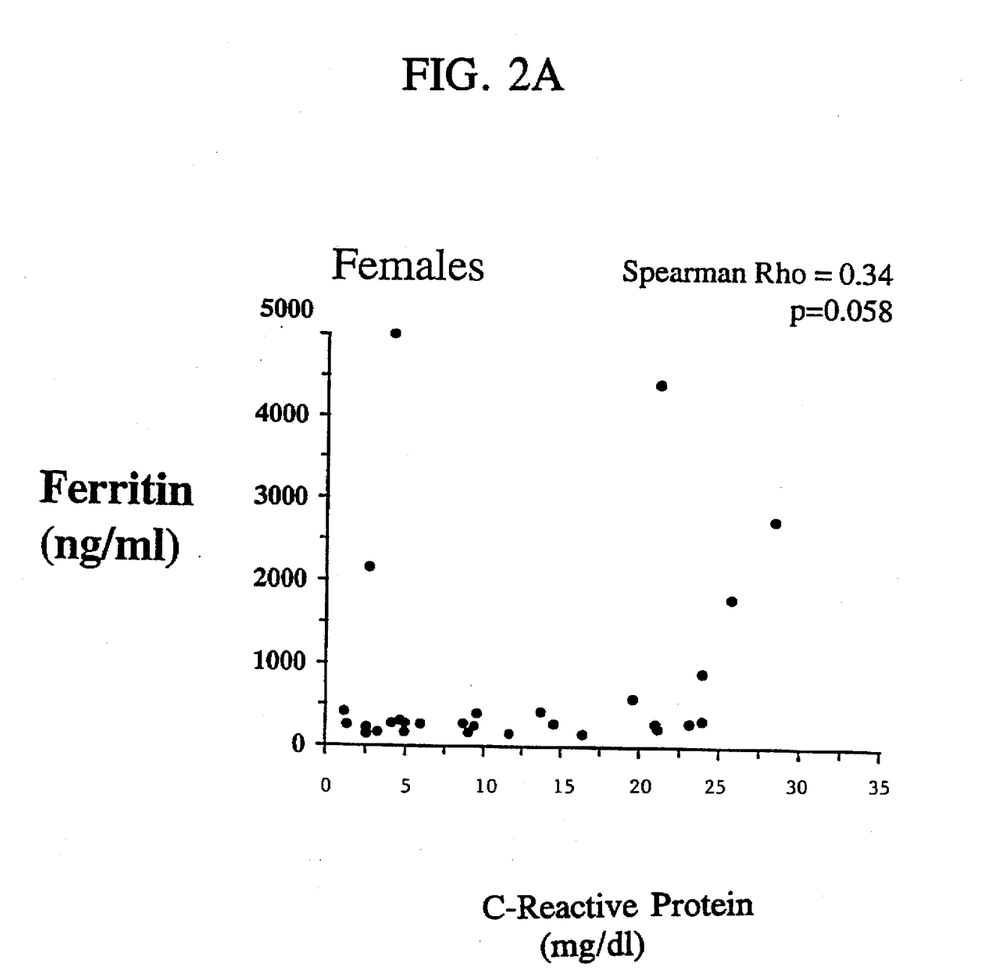
FIGS. 2A and 2B depict the relationship between simultaneous serum ferritin concentrations and C-reactive protein concentrations in at-risk females and males, respectively, for the development of ARDS.
Figure 2B:
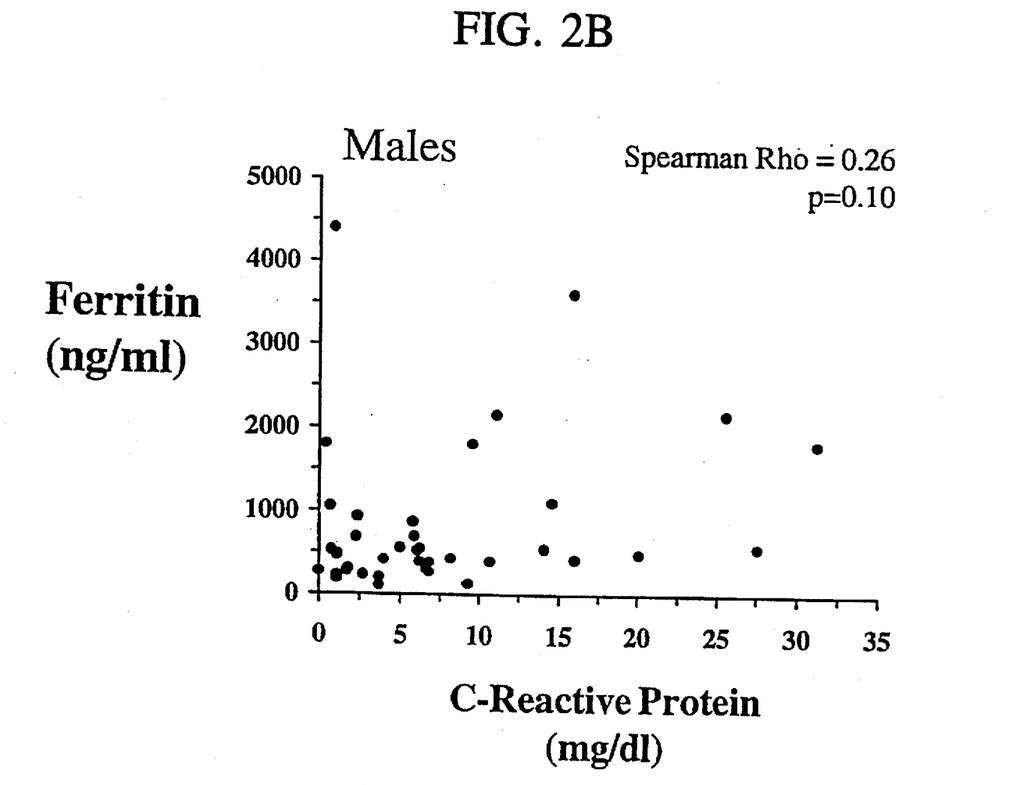

To control against the possibility that increases in serum ferritin concentration simply reflected a broader acute phase reaction, simultaneous serum concentrations of C-reactive protein (an acute phase marker) were determined on serum from 63 at-risk patients. Although C-reactive protein concentrations were elevated in our at-risk patients [normal range in our laboratory 0.5–2.2 mg/dl; median in at-risk, non-ARDS patients 6.6 mg/dl (25–75% quartiles 2.6–14.1); median in at-risk, pre-ARDS patients 6.8 mg/dl (25–75% quartiles 3.15–21.7)], there was no correlation with serum ferritin concentrations in either women or men (FIGS. 2A and 2B).

To determine the potential confounding role of liver disease, a multivariate logistic regression model was fit for the development of ARDS. The effects of serum ferritin, liver disease, and ethanol abuse (as a potential marker for liver disease) were studied in a stepwise manner using logistic regression analysis [Forthofer and Lee, supra, Chapter 15; Gore (1981), supra]. Although interaction terms were not tested due to limited sample size, in this model the effect of serum ferritin in women remained significant with a p=0.008, and an odds ratio of 13.11 (95 percent confidence intervals: 2.30 –118.76). Similarly, in men the effect of serum ferritin remained significant with a p=0.0007, and an odds ratio of 20.59 (95 percent confidence intervals: 4.06–146.46).

The foregoing data demonstrates that serum ferritin concentration is an effective determinant of ARDS development potential in this large, diverse population of at-risk patients, distinguishing at-risk, pre-ARDS patients from at-risk, non-ARDS patients who were otherwise identical with respect to risk factors and severity of illness as judged by APACHE II score. Moreover, serum ferritin measurements may be obtained non-invasively, which has obvious advantages over competing methods which require bronchoalveolar lavage.

It will be understood that, while serum ferritin concentrations of 270 ng/ml (woman) and 680 ng/ml (men) were selected as optimal discriminating concentrations and serve to define practical threshold (cut-off) concentrations (i.e., >270 ng/ml for women and >680 ng/ml for men) in a serum ferritin test for predicting ARDS development, other serum ferritin concentrations provide useful predictive value as well. The sensitivity, specificity, positive and negative predictive values, and accuracy for such other serum ferritin concentrations are determined in the same manner using the same art-recognized statistical analyses as described herein. For certain patient screening applications, including applications wherein multiple ARDS predictive markers are employed, it may be desirable to preference particular statistical parameters (e.g., sensitivity or specificity) over other statistical parameters when selecting a reference serum ferritin concentration as a cut-off concentration for predicting that a patient will develop ARDS. Moreover, it will be understood by one of ordinary skill in the an that the foregoing example may be repeated with selected patient subpopulations (e.g., selected based upon age, ARDS risk category, and/or other identifiable patient traits), and that the optimal discriminating serum ferritin concentration (when determined in the manner described above) may vary from the aforementioned selected values. Finally, it will be understood that the foregoing optimal discriminating serum ferritin concentrations were selected from data from a finite sample size, and that different optimal discriminating concentrations might be selected from data from a larger population of at-risk patients.

EXAMPLE 2

The following prospective example is conducted to determine an optimal battery of serum markers that, in combination, enhance the ability to predict the likelihood that an at-risk patient will develop ARDS.

Patients are selected as described in the preceding example. Within six hours of enrollment, each patient's blood is collected and serum is separated therefrom by centrifugation at 1000×g for ten minutes. The serum is stored at −70° C. if not analyzed immediately.

Serum ferritin is assayed as described in the preceding example or using other methods apparent to those of ordinary skill. Serum manganese superoxide dismutase (MnSOD) [U.S. Pat. Nos. 5,389,522 and 5,147,783; Kawaguchi et al., *Biochem. Biophys. Res. Comm.* (1990); 171(3):1378–1386], catalase and/or catalase activity [U.S. Pat. No. 5,389,522 and 3,926,732; Leff et al., *J. Appl. Physiol.* (1991); 71(5):1903–1906; Wiemer et al., *J. Immunol. Methods* (1992); 151:165–175], Factor VIII antigen [Cejka, *Clin. Chem.* (1982); 28(6):1356–58; U.S. Pat. Nos. 5,196,311 and 5,202,264], and lactate dehydrogenase (LDH) [Beutler, *A Manual of Biochemical Methods* (1984); Grune & Stratton, Inc., pp. 65–66] are assayed using materials and protocols known in the art. See generally Leff et al. (1993), supra.

The predictive value of the foregoing ARDS serum markers are analyzed alone and in various combinations using statistical approaches known in the art, including but not limited to the statistical methods described in the preceding example. The analyses are repeated for discrete patient sub-populations (e.g., sex, predisposing risk factors, age, etc.). Combinations of markers are selected to optimize, e.g., the accuracy with which one may predict the development of ARDS in patients at risk for developing ARDS.

EXAMPLE 3

The following prospective example is performed to demonstrate the ARDS predictive value of ferritin concentration in bronchoalveolar lavage fluid (BALF) of patients at risk for ARDS development, alone or in combination with markers described in previous examples. Although bronchoalveolar lavage is more invasive than serum (blood) collection, BALF has been shown to contain protein markers for ARDS development where serum measurements of the same protein are not predictive of ARDS. [See, e.g., Donnelly et al. (1993), supra (BALF IL-8 concentration predictive of ARDS development but serum IL-8 concentration not predictive)]. Thus, BALF ferritin concentration (alone or in combination with serum ferritin concentration and/or other serum or BALF ARDS markers) may provide different, and potentially enhanced, predictive value with respect to ARDS development in at-risk patients.

Patients are selected as described in Example 1 and bronchoalveolar lavage is performed (and the resultant BALF processed) using techniques known in the art [See e.g., Donnelly et al. (1993); Krsek-Staples et al., *Am. Rev. Respir. Dis.* (1992); 145:1009–1015]. Ferritin and other potential ARDS markers in BALF are assayed as described in the preceding examples or adapting methods known in the art. [See, e.g. Donnelly et al. (1993) (IL-8 assay)].

The predictive value of BALF ferritin concentrations and/or other potential BALF protein markers (alone or in combination with each other and serum protein markers), are determined statistically as described in the preceding examples. Combinations of markers are selected which provide enhanced ARDS predictive value as compared to individual serum markers.

While the present invention has been described in terms of specific embodiments, it is understood that variations and modifications will occur to those skilled in the art. Accordingly, only such limitations as appear in the appended claims should be placed on the invention.

What is claimed is:

1. A method for determining acute respiratory distress syndrome (ARDS) development potential in a patient at risk for the development of ARDS comprising the steps of determining the patient's sex and serum concentration of ferritin; comparing the patient's serum concentration of ferritin to a cut-off concentration of serum ferritin for the patient's sex, and determining ARDS development potential in said at-risk patient from the comparison, wherein serum concentrations of ferritin above the cut-off concentration for the patient's sex are predictive of ARDS development in the patient.

2. The method of claim 1 wherein the patient at risk for the development of ARDS has an ARDS predisposing condition selected from the group consisting of sepsis, severe pancreatitis, recent hypertransfusion, recent aspiration, severe abdominal trauma, severe chest trauma, and multiple fractures.

3. The method of claim 2 wherein the ARDS predisposing condition is sepsis.

4. The method of claim 2 wherein the ARDS predisposing condition is recent hypertransfusion.

5. The method of claim 1 wherein the sex of the patient is male and the cut-off concentration of serum ferritin is 680 nanograms of ferritin per milliliter of serum.

6. The method of claim 1 wherein the sex of the patient is female and the cut-off concentration of serum ferritin is 270 nanograms of ferritin per milliliter of serum.

7. A method for determining an at-risk patient's potential for developing acute respiratory distress syndrome (ARDS), the patient being of a predetermined sex, comprising the steps of determining said patients's serum concentration of ferritin, comparing said patient's serum concentration of ferritin to the serum concentration of ferritin of healthy human subjects having the same sex as the patient, and determining ARDS development potential from said comparison.

8. A method for determining acute respiratory distress syndrome (ARDS) development potential in a patient at risk for the development of ARDS comprising the steps of:

determining the serum concentration of ferritin in the at-risk patient, determining the serum level of at least one additional ARDS marker selected from the group consisting of manganese superoxide dismutase (MnSOD), catalase, lactate dehydrogenase (LDH), and Factor VIII antigen in the at-risk patient, and determining the ARDS development potential in the at-risk patient from said serum concentration of ferritin and said serum level of said additional selected ARDS marker or markers.

9. The method of claim 8 wherein the at-risk patient is a septic patient.

10. The method of claim 9 wherein the additional selected ARDS marker is LDH.

11. The method of claim 9 wherein the additional selected ARDS marker is MnSOD.

12. The method of claim 10 wherein the additional selected ARDS marker is catalase.

13. A kit for determining acute respiratory distress syndrome (ARDS) development potential in an at-risk patient from the patient's serum comprising, in association, a means for determining serum ferritin concentration, and at least one of the following:

(a) a means for determining a serum level of manganese superoxide dismutase (MnSOD);

(b) a means for determining a serum level of lactate dehydrogenase (LDH);

(c) a means for determining a serum level of serum Factor VIII antigen; and (d) a means for determining a serum level of catalase.

14. The kit of claim 13 comprising a means for determining serum ferritin concentration, and a means for determining serum MnSOD concentration.

15. The kit of claim 13 comprising a means for determining serum ferritin concentration, and a means for determining serum LDH concentration.

16. The kit of claim 13 comprising a means for determining serum ferritin concentration, and a means for determining serum catalase activity.

17. A kit for determining the acute respiratory distress syndrome (ARDS) development potential in an at-risk patient from the patient's serum comprising a means for determining a serum ferritin concentration from the serum of an at-risk patient, and a means for determining ARDS development potential in said at-risk patient from said serum ferritin concentration.

18. In a kit for determining a patient's serum ferritin concentration, the improvement comprising including in said kit a means for determining acute respiratory distress syndrome (ARDS) development potential in an at-risk patient from said at-risk patients' serum ferritin concentration.

* * * * *